United States Patent [19]

Layton et al.

[11] Patent Number: 4,931,384
[45] Date of Patent: Jun. 5, 1990

[54] OPTICAL ASSAY TECHNIQUE

[75] Inventors: Derek G. Layton, Cambridge; Alan M. Smith; John H. Fisher, both of Royston; Robert M. Pettigrew, Cambridgeshire; Satham Petty-Saphon, Saffron Waldon, all of England

[73] Assignee: Ares-Serono N.V., Geneva, Switzerland

[21] Appl. No.: 643,141

[22] Filed: Oct. 17, 1984

Related U.S. Application Data

[63] Continuation of PCT GB83/00340 filed Dec. 21, 1983, published as WO84/02578 on July 5, 1984.

[30] Foreign Application Priority Data

Dec. 21, 1982 [GB] United Kingdom ............ 8236333
Jan. 14, 1983 [GB] United Kingdom ............ 8301021

[51] Int. Cl.$^5$ .................. G01N 33/535; G01N 33/553
[52] U.S. Cl. ........................................ 435/7; 435/805;
435/808; 436/518; 436/525; 436/531; 436/164;
436/171; 436/548; 436/805; 436/810; 356/317;
356/318; 356/305; 250/461.1; 250/461.2
[58] Field of Search ............ 436/518, 524, 527, 528,
436/536, 537, 163, 805, 810, 73, 74, 164, 171,
525, 531, 548; 356/317, 318, 417, 461.1, 461.2,
305; 435/7, 805, 808; 427/2

[56] References Cited

U.S. PATENT DOCUMENTS

| | | | |
|---|---|---|---|
| 3,853,467 | 12/1974 | Giaever | 435/5 |
| 3,926,564 | 12/1975 | Giaever | 422/57 |
| 3,939,350 | 2/1976 | Kronick et al. | 436/527 |
| 3,979,184 | 9/1976 | Giaever | 422/57 |
| 4,011,308 | 3/1977 | Giaever | 436/525 |
| 4,041,146 | 8/1977 | Giaever | 424/7 |
| 4,050,895 | 9/1977 | Hardy | |
| 4,054,646 | 10/1977 | Giaever | 424/12 |
| 4,090,849 | 5/1978 | Healy et al. | 424/12 |
| 4,222,743 | 9/1980 | Wang | |
| 4,521,522 | 6/1985 | Lundström et al. | 435/525 |
| 4,558,012 | 12/1985 | Nygren et al. | 436/518 |
| 4,647,544 | 3/1987 | Nicoli et al. | 436/518 |

FOREIGN PATENT DOCUMENTS

| | | |
|---|---|---|
| 0073980 | 3/1983 | European Pat. Off. |
| 81/00912 | 4/1981 | PCT Int'l Appl. |
| 1486826 | 9/1977 | United Kingdom |
| 1564333 | 4/1980 | United Kingdom |
| 83/01112 | 3/1983 | World Int. Prop. O. |

Primary Examiner—Esther M. Kepplinger
Attorney, Agent, or Firm—Merchant, Gould, Smith, Edell, Welter & Schmidt

[57] ABSTRACT

An assay technique for qualitative and quantitative detection of a chemcial, biochemical or biological detection of a chemical, biochemical or biological species in sample. The technique comprises (a) coating at least a predetermined part of a pre-formed surface on a substrate with a thin film of a material capable of binding the species to be assayed, the pre-formed surface being optically active with respect to radiation at least over a predetermined band of wavelengths; (b) contacting the coated surface with sample; and (c) observing the optical properties of said pre-formed surface in order to determine a qualitative and quantitative change in optical properties as a result of the binding of the species onto said thin film of material. The optical properties of the pre-formed surface may be observed before and after step (b) in order to determine any change in optical properties, or they may be monitored during step (b). The pre-formed surface is preferably a grating. An article for use in the above technique is also disclosed, and comprises a substrate carrying said pre-formed surface which in turn is coated with the respective material for the species to be assayed.

82 Claims, 2 Drawing Sheets

OPTICAL ASSAY TECHNIQUE

This is a continuation of application Ser. No. PCT GB83/00340, filed Dec. 21, 1983, published as WO84/0257 on July 5, 1984.

This invention relates to an assay technique for qualitative and/or quantitative detection of chemical, biochemical or biological species in a sample.

The technique is based upon the affinity of the species which is to be assayed for a receptive material, for example a ligand or a specific binding partner, which receptive material is coated onto a particular type of surface.

More particularly, according to one aspect of the present invention, there is provided an assay technique for qualitative and/or quantitative detection of a chemical, biochemical or biological species in a sample, which comprises (a) coating at least a predetermined part of a pre-formed surface on a substrate with a thin film of a material capable of binding the species to be assayed, the pre-formed surface being optically active with respect to radiation at least over a predetermined band of wavelengths; (b) contacting the coated surface with the sample; and (c) observing the optical properties of said pre-formed surface in order to determine a qualitative and/or quantitative change in optical properties as a result of the binding of the species onto said thin film of material.

In a first embodiment of the method of this invention, the optical properties of the pre-formed surface are observed before and after step (b) in order to determine any change in optical properties as a result of the species being bound by the receptive material in the thin film coating on the pre-formed surface. In a second embodiment, the optical properties of the pre-formed surface are monitored during step (b) in order to determine the said change in optical properties.

According to a second aspect of the present invention, there is provided an article for use in an assay technique as defined above, which article comprises a substrate having a pre-formed surface which is optically active with respect to radiation at least over a predetermined band of wavelengths, and at least a predetermined part of which pre-formed surface is coated with a thin film of a material capable of binding a predetermined chemical, biochemical or biological species.

The pre-formed surface is preferably a grating. A single grating may be employed, or the surface may comprise two or more gratings disposed mutually at an angle. Where there are two such gratings, they may be mutually orthogonal. The profile of the or each grating is advantageously square-wave or sinusoidal. Saw-tooth profiles are also possible, but are not presently preferred.

The pre-formed surface may alternatively comprise a regular array of protuberances. With a surface of this type, and the alignment of the peaks of the protuberances and the troughs between the protuberances corresponds to the ridges and troughs of a grating-type structure.

The thin film of receptive material may be coated onto the pre-formed surface so as to be deposited only in the troughs of the grating or in the troughs between the protuberances. A monomolecular layer of the receptive material will suffice and will generally be preferred, whether or not the coating is confined to the troughs.

The surface structure of the pre-formed surface and in particular the dimensions of the surface relief pattern will be selected according to the nature of the species which is to be assayed. In general, we have found three ranges of surface depth (peak-to-trough measurements) to be advantageous. In the first, the grating or protuberance or each of the gratings or protuberances, in the event several are employed, have a depth in the range 10 to 50 nanometers. In the second, the depth is in the range 50 to 200 nanometers; and in the third, the depth is in the range 200 to 2000 nanometers. With the first of these ranges, the pitch (period) of the each grating(s) or the periodicity of the protuberances is advantageously greater than their depth; the structure thus corresponds, in general, to that of a shallow grating. With the second and third ranges, the pitch (period) of the or each grating or the periodicity of the protuberances is advantageously of the same order as their depth.

In a first group of embodiments, the pre-formed surface is structured so that it is optically active with respect to radiation whose wavelength is in the range from 700 to 1500 nanometers. In a second group of embodiments, the pre-formed surface is structured so that it is optically active to radiation whose wavelength falls within the range from 350 to 700 nanometers.

Conveniently, the substrate which carries the pre-formed surface is formed of a plastics material. Plastics materials curable by ultra-violet light are preferred, and in particular acrylic or polyester materials can advantageously be used. A presently preferred plastics material is polymethylmethacrylate. A plastics substrate for use in this invention preferably has a refractive index in the range 1.25 to 1.6, and more preferably a refractive inded of about 1.4.

An alternative substrate is a glass coated with a synthetic polymeric material.

The active surface of the substrate (i.e., that surface which is, or which carries, the pre-formed surface) can be constituted by a metal or a metal layer. Thus a plastics substrate, e.g., of polymethylmethacrylate, can have adhering thereto a metal layer which constitutes the pre-formed surface (e.g. a single grating structure of depth about 250 nanometers and period about 400 nanometers). With such a structure, the plastics/metal interface may be planar, or it may conform to the surface structure of the metal layer itself. The metal used to form such layers may be gold, silver, copper or aluminium. Alternatively, the active surface of the substrate may be constituted by an inorganic oxide or a layer thereof. The inorganic oxide is advantageously an oxide of silver, copper or aluminium. Such an oxide layer may be produced by causing or allowing oxidation of the surface of a metal substrate or of a metal layer adhering to a substrate of a different material. Where there is a layer of metal or of an inorganic oxide as just described, the layer is preferably from 5 to 50, more preferably 10 to 30, nanometers thick.

Conveniently, the substrate is lamellar and in strip-form. This facilitates use of an article in accordance with the invention in carrying out the assay.

The observation of optical properties in step (c) of the method of this invention can take place in transmission or in reflection. One zone of the pre-formed surface on the substrate may be left free of the coating of receptive material; the method may be performed by keeping this one zone free from sample, in step (b), or by contacting the whole of the pre-formed surface, including said one zone, with the sample. This latter technique has advantages in that any optical effects caused by components of the sample other than the species to be assayed will affect the coated and uncoated zones equally, and thus will cancel each other out when a comparison between the coated and non-coated zones is made. A two-beam illuminating system can be employed in step (c) of the method, one of the beams being directed at the uncoated zone of the pre-formed surface, and the other of the two beams being directed at a part of the coated zone of the pre-formed surface. Preferably, monochromatic radiation is used.

When the substrate and the pre-formed surface are constituted by a plastics material, and observations of the optical properties of the surface are to be carried out in transmission, it is preferred that the uncoated, pre-formed surface when viewed in transmission normal to the plane of the surface should have a transmission not exceeding 1% for the radiation which is to be used.

In order to give optimum results when the technique of this invention is used for quantitative analysis, it may be advantageous to calibrate the coated substrate by first carrying out the assay technique using a sample containing a known proportion of the species which is to be assayed.

The present invention is applicable, for example, to testing a biological liquid, e.g. a blood sample, for specific antigen molecules. In such a case, the receptive material capable of binding the species to be assayed will comprise antibodies for the antigen concerned. Alternatively, it is possible to use an antigen as the receptive material and to assay a sample for antibodies. Where the receptive material comprises antibodies, these are preferably monoclonal antibodies. Antigens and antibodies occur in a wide range of molecular dimensions, and the surface structure of the pre-formed surface will be determined in part by the size of the molecules concerned. As an example, antigens resulting from many parasitic infections are typically in the size range from about 0.5 microns to 10 microns; for these antigens, a grating pitch of greater than 6 microns and preferably greater than 10 microns is desirable. In general, a grating pitch of the order of twice the antigen size will be desirable.

The invention is also applicable to the assaying of other chemical, biochemical or biological species, for example ionic species. The invention may be used, for example, to assay the metal ion content of a sample. The receptive material may be, for example, a chelating chemical or enzyme or a chelating organism which constitutes a specific binding partner for the ligand or ion which is to be assayed. In general the chemical, the enzyme or organism will be one or more of: a polypeptide, a steroid, a saccharide or polysaccharide, a proteoglycan, a nucleotide, a nucleic acid, a protonucleic acid, a microbial cell or a yeast.

Application of the invention thus lies not only in the medical field for diagnostics, but also generally in the field of process control.

The thin film of receptive material is preferably bonded firmly to the pre-formed surface of the substrate. Thus the receptive material may be bonded by electrostatic or covalent bonding to said surface.

Observations in step (c) of the method of this invention may use polarised light. In one particular technique, the pre-formed surface of the substrate is in the form of a single grating of square-wave or sinusoidal profile, and the optical properties of the surface are observed, in step (c), by monitoring the angular position at which there occurs a sharp reduction (dip) in reflection as the surface is observed or scanned with polarised radiation of a predetermined wavelength. The radiation used is preferably light, and the polarisation should be transverse to the grooves of the grating.

A presently preferred article in accordance with this invention consists of a profiled plastics strip, desirably fabricated by an embossing or casting technique, and with a refractive index of the order of 1.4 and a transmission not exceeding 1%. The strip profile may be that of a single grating with square grooves, dimensioned for zero order suppression over a range of wavelengths. However, other profiles and dimensions can be used if desired, enabling diffraction efficiency into particular orders to be enhanced or suppressed.

An article in accordance with this invention may have a plurality of zones, each of which is coated with a different receptive material. In this way, a single article, e.g. in the form of a strip, can be used to assay a plurality of different species, e.g. antigens in a blood sample or metal ions in a biochemical fluid or in an industrial effluent.

In the case of a square profile grating, if the pitch is d, the groove height h and the refractive index n, then zero order diffracted light of wavelength W will be suppressed for $h = W/2(n-1)$, whilst first order diffracted light will emerge at angles given by $\sin O = \pm W/d$. For application to blood sampling, given a grating pitch of about 6 microns, and a source wavelength of 550 nm (green), then $h = 0.69$ microns; $O = \pm 5.2°$.

The principle of the assaying method is that the receptive material, e.g. antibodies, coated on the grating are typically small molecules, e.g. sized around 10 nm, and are too small to produce any size or shape dependent light scattering. However, the antigens attached to the antibodies when a blood sample is smeared on the grating have a size of the same order as the wavelength of incident light, and have an effect analogous to that of filling some of the grating grooves with water (refractive index 1.33). This means that, in the case of a grating dimensioned as above, zero order light is no longer suppressed, whilst very little light is diffracted into the higher orders. Generally, therefore, the transmission of the grating, normally not exceeding 1%, will be directly related to the number of antigens present.

The method thus depends on determination of the change in optical properties, e.g. transmission or reflection characteristics, of the grating. For this reason, given a grating coated with antibodies over its whole area, the smearing of a part of this area with the sample can readily enable the said change to be quantitively determined. A similar effect is preferably achieved, however, by coating only a part of the grating with antibodies, as the antigens will not be attracted into and trapped in the grooves in the uncoated region. Preferably, in conjunction with the last mentioned partly coated grating, a two beam illuminating system will be employed. The source may be an incandescent lamp emitting light incident on the grating through a filter. The angle of incidence of the monochromatic (or nearly monochromatic) light on the grating is preferably 0° (i.e. normal to the grating) and, for the grating exemplified above, zero order diffracted light would be collected by means of a lens onto a photodetector, while higher order diffracted light would be obscured using a stop.

One aim of the invention is to provide a low cost pre-coated grating which can be widely used for diagnostic purposes, commonly in a general practitioner's surgery but possibly also in the home. For this purpose, the antibodies would be firmly bonded to the plastics grating, e.g. by electrostatic bonding which can ensure virtually permanent coating provided that a suitable or suitably treated plastics material is initially chosen to form the grating. As the aim would usually be to detect a specific antigen, the grating would be coated with a specific antibody, e.g. a monoclonal antibody which attracts and retains only the specific antigen in question. Thus, successive testing of a plurality of selectively coated gratings would enable quantitative detection of specific antigens as an aid to diagnosis.

The technique of smearing the grating with the sample also requires consideration. After wiping the grating with, say, a blood sample, it is important to remove any excess sample in order to ensure that minimum carrier liquid, minimum haemoglobin and minimum large cells other than antigen are retained.

As the effect of absorption by red cells containing haemoglobin can be minimised by suitable choice of the wavelength of illumination, it is the retention of carrier liquid which is the next likely source of errors of detection. For minimising such errors, the grating may be dimensioned for zero order suppression when there is a continuous liquid film on top of the grating; this requires a modified grating height of $h = W/2 (n1 - n2)$, where $n1$ is the refractive index of the substrate and $n2$ is the refractive index of the liquid. A liquid of high refractive index is desirable, and one suitable example is glycerol. The smearing technique (i.e. step (b)) would then include the step of washing the grating, after wiping it with the sample, with the liquid in question.

A further point to be understood in connection with the smearing technique is that this will commonly result in only a small percentage, e.g. less than 2%, of the overall area of the grating bearing and retaining attracted antigens. The use of a diffractor grating of high sensitivity relieves the illuminating and detector system of the extreme requirements which would otherwise be required quantitatively to detect such a small presence of antigen, thus making practical the use of relatively simple and low cost optics which can enable widespread use.

One example of assaying method and apparatus in accordance with the invention is shown in the accompanying drawing, in which.

Figure 2:
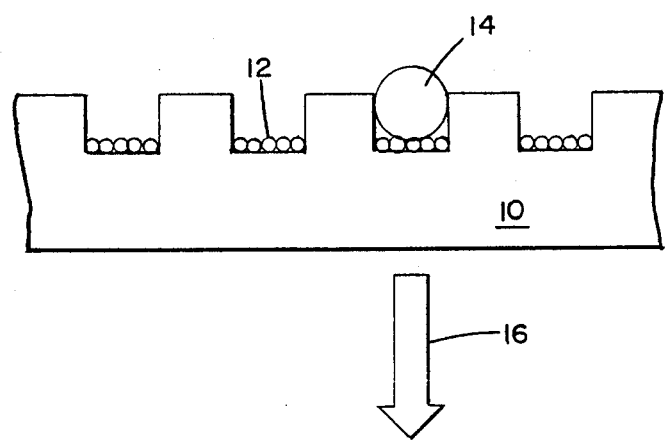
FIG. 2 shows a detail of one embodiment of an article incorporating a diffraction grating and forming part of the system of FIG. 1.

Referring first to FIG. 2, a square profile single diffraction grating 10 whose pitch and depth are both equal to 800 nanometers is coated with a substantially mono-molecular layer of immobilised antibodies 12, preferably monoclonal antibodies. After smearing with a sample, an antigen 14, being a binding partner to the antibodies, is attracted and trapped in one groove. At this point of the grating, the zero order diffracted light is transmitted, as indicated at 16, instead of being suppressed.

Figure 1:
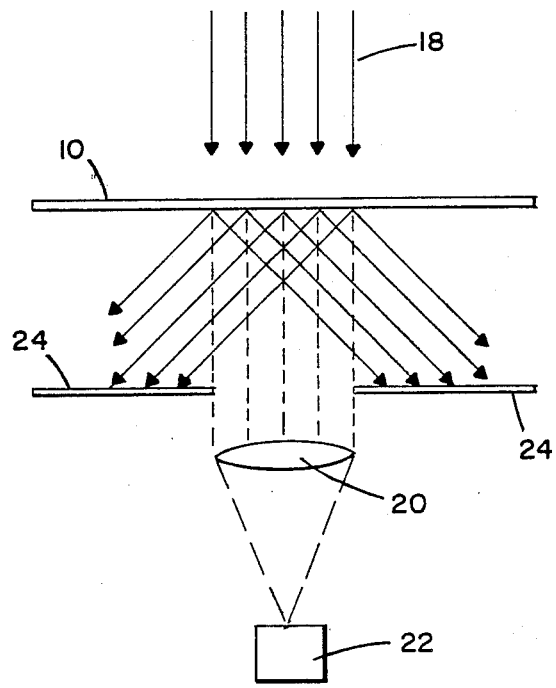
FIG. 1 shows an optical illuminating and detecting system.

FIG. 1 shows the grating 10 under illumination by monochromatic light 18. Zero order diffracted light is collected by a lens 20 onto a photodetector 22, while higher order diffracted light is obscured by a stop 24. A two-beam illuminating system which, as described above, is generally preferred, will operate in a precisely analogous way.

Figure 3:
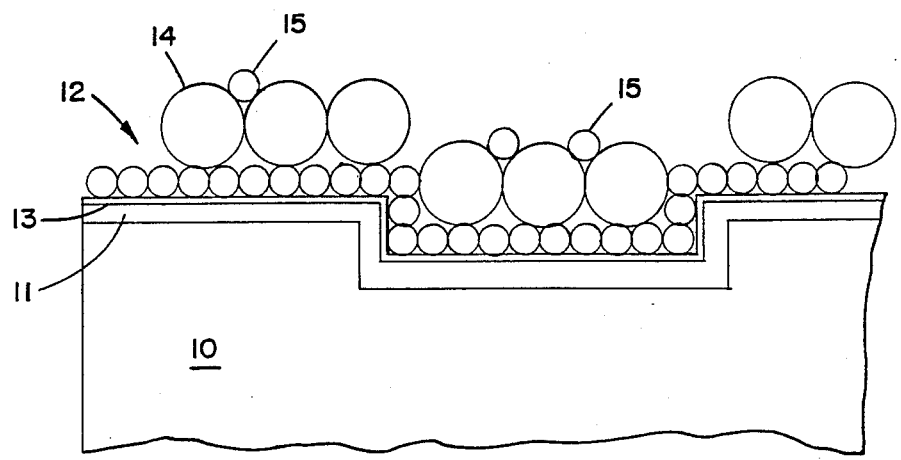
FIG. 3 shows a cross-sectional view (not to scale) of a second embodiment of an article incorporating a diffraction grating.
Figure 4:
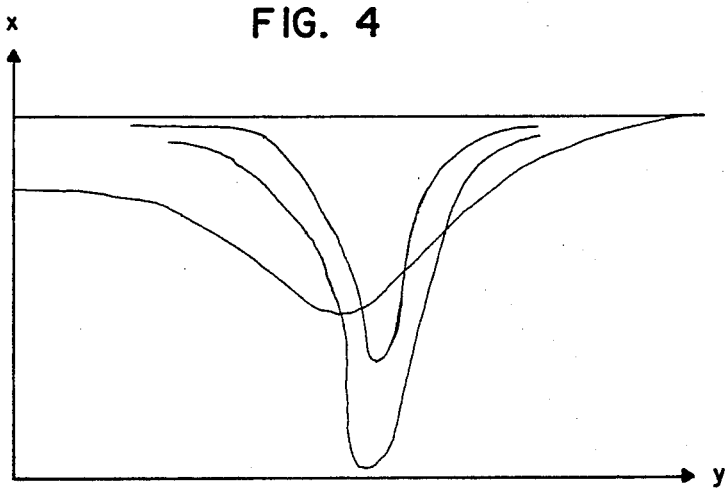
FIG. 4 illustrates the results obtained with an article of the type illustrated in FIG. 3. The x-axis represents the Reflectivity and the y-axis represents the Angle of Incidence.

Referring next to FIG. 3, an article in accordance with this invention is shown in the condition after it has been contacted by a sample in step (b) of the method of the invention. The article comprises a substrate 10 formed of polymethylmethacrylate which is about 1 millimeter thick. The active (upper) surface of the substrate includes a layer 11 of aluminium of thickness 20 nanometers. This is covered by a passive film 13 of aluminium oxide (thickness one nanometer or less). A monomolecular layer of antigen molecules 12 is covalently bonded to the film 13 of aluminium oxide and is thus immobilised. A layer of antibodies 14 is attached to the antigen layer 12. This layer 14 is also monomolecular and is about ten nanometers thick. Isolated antigens 15 have been bound by the antibodies 14. The substrate 10 with the layers 11, 13, 12 and 14 constitutes one embodiment of the article of this invention. The preformed surface is in effect defined by the surface of layer 13; this is in the form of a single grating of depth 50 nanometers and of pitch (period) 250 nanometers. The article is observed, in carrying out the method of the invention, with monochromatic light which is polarised in a plane perpendicular to the lines of the grating; the angle of incidence of the illumination is varied and it is found that there is a sharp reduction (dip) in reflectivity at an angle whose value depends upon the amount of material (antibodies 14) overlying the article. The angular position of this dip, and also its angular width, are strongly dependent upon the amount of antigens attached to the layer 14 of antibodies and hence these parameters provide a quantitative measure of the antibodies absorbed from the sample. FIG. 4 plots the reflectivity of the article against the angle of incidence of the monochromatic, polarised illumination over a small angular range. As the quantity of antigens captured by the antibody layer 14 increases, the dip in reflectivity first of all becomes more pronounced, and then becomes broader and the angular position of the reflectivity minimum alters, as shown in the three curves plotted. The reflectivity dip can be considered theoretically as a plasmon resonance; it is relatively easy to detect a change in the angle of incidence of about 0.1 degrees or a change in the wavelength of the resonance by about 1 nanometer. Hence it is possible to detect changes corresponding to an increase in the average thickness of the antigen layer 15 of around one nanometer. It will be appreciated that, when antigens are bound by the layer 14, the result is not the addition of a further layer of uniform thickness; nevertheless, we have found that the occurrence of isolated antigens 15 over the layer 14 of antibodies behaves approximately as though they were "smoothed out" into a layer whose average thickness modifies the optical properties of the system as a whole.

We claim:

1. An assay technique for qualitative and quantitative detection of a chemical, biochemical or biological species in a sample, which comprises:

(a) coating at least a predetermined part of a surface having a pre-formed regular periodic surface structure provided on a substrate with a thin film of a material capable of binding the species to be assayed, said surface producing a reflective dip with respect to a parameter of incident polarized light;

(b) contacting the coated surface with the sample;

(c) directing polarized light at said coated surface; and (d) measuring the change in the reflective dip as a result of the binding of the species onto said thin film of material, whereby a quantitative measure of the species being assayed is provided.

2. A method according to claim 1, wherein the reflective dip is measured before and after step (b) in order to determine the said change.

3. A method according to claim 1, wherein the reflective dip is monitored with respect to changes in the angle of incidence or wavelength of the incident polarized light.

4. A method according to claim 1, wherein said pre-formed regular periodic surface structure is a diffraction grating.

5. A method according to claim 4, wherein the grating is of square-wave profile.

6. A method according to claim 4, wherein the grating is of sinusoidal profile.

7. A method according to claim 4, wherein the grating is of saw-tooth profile.

8. A method according to claim 4, wherein the grating has a depth (peak-to-trough) in the range 10 to 50 nanometers.

9. A method according to claim 8, wherein the pitch (period) of the grating is greater than its depth.

10. A method according to claim 4, wherein the grating has a depth (peak-to-trough) in the range 50 to 200 nanometers.

11. A method according to claim 10, wherein the pitch (period) of the grating is of the same order as its depth.

12. A method according to claim 4, wherein the grating has a depth (peak-to-trough) in the range 200 to 2000 nanometers.

13. A method according to claim 1, wherein said pre-formed regular periodic surface structure comprises two or more diffraction gratings disposed mutually at an angle.

14. A method according to claim 1, wherein said surface is structured so that it is reflective with respect to radiation of wavelengths from 700 to 1500 nanometers.

15. A method according to claim 1, wherein said surface is structured so that it is reflective with respect to radiation of wavelengths from 350 to 700 nanometers.

16. A method according to claim 1, wherein at least the active surface of the substrate is comprised of a metal or a metal layer.

17. A method according to claim 16, wherein said metal is gold, silver, copper or aluminum.

18. A method according to claim 1, wherein the active surface of the substrate is comprised of an inorganic oxide or a layer thereof.

19. A method according to claim 18, wherein said inorganic oxide is an oxide of silver, copper or aluminum.

20. A method according to claim 1, wherein the substrate is in strip-form.

21. A method according to claim 1, wherein one zone of said surface distinct from said predetermined part of the surface on the substrate is left free of the coating material and is not contacted, in step (b), by the sample.

22. A method according to claim 21, wherein a two-beam illuminating system is employed in step (c), one of said beams being directed at said one zone of said surface, and the other of the two beams being directed at said predetermined surface part.

23. A method according to claim 1, wherein one zone of said surface distinct from said predetermined part of the surface is left free of the coating material and the whole of said surface, including said one zone, is contacted, in step (b), by the sample.

24. A method according to claim 3 wherein the polarized light is monochromatic and the parameter of the light monitored is its angle of incidence.

25. A method according to claim 1, wherein the species which is to be detected is an antigen.

26. A method according to claim 25, wherein the material capable of binding said species comprises antibodies for the antigen which is to be assayed.

27. A method according to claim 26, wherein said antibodies are monoclonal antibodies.

28. A method according to claim 11, wherein the species which is to be assayed is an ionic species.

29. A method according to claim 28, wherein said ionic species is a metal ion.

30. A method according to claim 28, wherein the material capable of binding the species to be assayed is a chemical, enzyme or a organism.

31. A method according to claim 30, wherein said chemical, enzyme or organism is one or more of: a polypeptide, a steroid, a saccharide or polysaccharide, a proteoglycan, a nucleotide, a nucleic acid, a protonucleic acid, a microbial cell or a yeast.

32. A method according to claim 1, wherein said thin film of material is firmly bonded to said surface.

33. A method according to claim 1, wherein said preformed regular periodic surface structure comprises a regular periodic array of protuberances.

34. A method according to claim 33, in which said surface is washed immediately after being contacted with the sample and before the observations in step (c).

35. A method according to claim 34, in which said surface is covered with a layer of a liquid of high refractive index between steps (b) and (c).

36. A method according to claim 1, in which said surface is washed immediately after being contacted with the sample and before the observations in step (d).

37. A method according to claim 36, in which said surface is covered with a layer of a liquid of high refractive index between steps (b) and (c).

38. An assay technique for qualitative and quantitative detection of a chemical, biochemical or biological species in a sample, which comprises:

(a) coating at least a predetermined part of a surface having a pre-formed single diffraction grating or two or more gratings disposed mutually at an angle provided on a substrate with a thin film of a material capable of binding the species to be assayed, said surface suppressing the transmission of zero-order diffracted light at least over a predetermined band of wavelengths;

(b) contacting the coated surface with the sample; and (c) measuring the change in transmission of zero-order diffracted light as a result of the binding of the species onto said thin film of material, whereby a quantitative measure of the species being assayed is provided.

39. A method according to claim 38, wherein the transmission of said surface is measured before and after step (b) in order to determine the said change in transmission.

40. A method according to claim 38, wherein the transmission of said surface is monitored during step (b) in order to determine the said change in transmission.

41. A method according to claim 38, wherein the grating is of square-wave profile.

42. A method according to claim 38, wherein the grating is of sinusoidal profile.

43. A method according to claim 38, wherein the grating is of saw-tooth profile.

44. A method according to claim 38, wherein the grating has a depth (peak-to-trough) in the range 10 to 50 nanometers.

45. A method according to claim 44, wherein the pitch (period) of each grating is greater than their depth.

46. A method according to claim 38, wherein the grating has a depth (peak-to-trough) in the range 50 to 200 nanometers.

47. A method according to claim 46, wherein the pitch (period) of each grating is of the same order as their depth.

48. A method according to claim 38, wherein the grating has a depth (peak-to-trough) in the range 200 to 2000 nanometers.

49. A method according to claim 38, wherein the substrate is formed of a plastic material.

50. A method according to claim 49, wherein said plastic material is a material which is curable by ultraviolet light.

51. A method according to claim 49, wherein said plastic material is an acrylic or a polyester material.

52. A method according to claim 51, wherein said plastic material is polymethylmethacrylate.

53. A method according to claim 49, wherein the plastic material has a refractive index in the range 1.25 to 1.6.

54. A method according to claim 53 wherein the refractive index of said plastic material is about 1.4.

55. A method according to claim 38, wherein the substrate is a glass coated with a synthetic polymeric material.

56. A method according to claim 38, wherein the active surface of the substrate is constituted by an inorganic oxide or a layer thereof.

57. A method according to claim 38, wherein the substrate is in strip-form.

58. A method according to claim 38 wherein one zone of said surface distinct from said predetermined part of the surface on the substrate is left free of the coating material and is not contacted, in step (b), by the sample.

59. A method according to claim 58, wherein a two-beam illuminating system is employed in step (c), one of said beams being directed at said one zone of said surface, and the other of the two beams being directed at said predetermined surface part.

60. A method according to claim 38, wherein one zone of said surface distinct from said predetermined part of the surface is left free of the coating material and the whole of said surface, including said one zone, is contacted, in step (b), by the sample.

61. A method according to claim 38, wherein in step (c) monochromatic radiation is used.

62. A method according to claim 38, wherein the species which is to be detected is an antigen.

63. A method according to claim 62, wherein the material capable of binding said species comprises antibodies for the antigen which is to be assayed.

64. A method according to claim 63, wherein said antibodies are monoclonal antibodies.

65. A method according to claim 38, wherein the species which is to be assayed is an ionic species.

66. A method according to claim 65, wherein said ionic species is a metal ion.

67. A method according to claim 65, wherein the material capable of binding the species to be assayed is a chemical, enzyme or a organism.

68. A method according to claim 67, wherein said chemical, enzyme or organism is one or more of: a polypeptide, a steroid, a saccharide or polysaccharide, a proteoglycan, a nucleotide, a nucleic acid, a protonucleic acid, a microbial cell or a yeast.

69. A method according to claim 38, wherein said thin film of material is firmly bonded to said surface.

70. An article for use in an assay technique for qualitative and quantitative detection of a chemical, biochemical or biological species in a sample, which comprises a surface with a regular periodic pre-formed surface structure reflective of polarized light at least over a pre-determined band of wavelengths, and said surface including a metal layer capable of supporting surface plasmon resonance, at least a pre-determined part of said surface including the metal layer being coated with a thin film of a material capable of binding the species to be assayed.

71. An article as claimed in claim 70, wherein the surface is lamellar.

72. An article as claimed in claim 24, wherein the surface is in strip-form.

73. An article as claimed in claim 70, wherein the preformed surface structure is a diffraction grating of square-wave, sinusoidal or saw-tooth profile.

74. An article as claimed in claim 70, wherein the preformed surface structure comprises a regular periodic array of protuberances.

75. An article as claimed in claim 70, wherein said metal is gold, silver, copper or aluminum.

76. An article as claimed in claim 70, wherein said surface is constituted by an inorganic oxide.

77. An article as claimed in claim 76, wherein said oxide is an oxide of silver, copper or aluminum.

78. An article as claimed in claim 70, wherein said thin film of material comprises antibodies.

79. An article as claimed in claim 70, wherein said thin film of material comprises a chemical enzyme or an organism.

80. An article as claimed in claim 70, wherein said surface is constituted by a layer at least 5 nanometers in thickness.

81. An article as claimed in claim 70, wherein the article includes a plurality of zones each of which is coated with a different receptive material so that the article is capable of binding a plurality of different species.

82. An assay technique for qualitative and quantitative detection of a chemical, biochemical or biological species in a sample, which comprises: (i) contacting the surface of an article as claimed in claim 70 with the sample; and (ii) measuring the change in surface plasmon resonance of the surface of said article as a result of the binding of the chemical, biochemical or biological species onto said surface whereby a quantitative measure of the species being assayed is provided.

* * * * *

UNITED STATES PATENT AND TRADEMARK OFFICE
CERTIFICATE OF CORRECTION

PATENT NO.  :   4,931,384
DATED       :   June 5, 1990
INVENTOR(S) :   Derek G. Layton, et al.

It is certified that error appears in the above-identified patent and that said Letters Patent is hereby corrected as shown below:

Title page, filing date item [21]: should be --Aug. 20, 1984--.

Column 1, line 6, "W084/0257" should be --W084/02578--

Column 2, line 33, "inded" should be --index--

Column 8, line 25, "11" should be --1--

Column 10, line 33, "24" should be --71--

Column 10, line 49, after "chemical" insert a comma

Signed and Sealed this

Seventeenth Day of May, 1994

Attest:

BRUCE LEHMAN

*Attesting Officer*    *Commissioner of Patents and Trademarks*